United States Patent [19]

Weil

[11] 4,051,201

[45] Sept. 27, 1977

[54] THIOBISPHENOL ESTERS OF PENTAVALENT PHOSPHORUS ACIDS

[75] Inventor: Edward D. Weil, Hastings-on-Hudson, N.Y.

[73] Assignee: Stauffer Chemical Company, Westport, Conn.

[21] Appl. No.: 598,297

[22] Filed: July 23, 1975

Related U.S. Application Data

[63] Continuation of Ser. No. 26,060, April 6, 1970, abandoned.

[51] Int. Cl.² .......................... C07F 9/09; C10M 1/48
[52] U.S. Cl. .................................. 260/930; 252/46.6; 260/968
[58] Field of Search ................. 260/968, 949, 930

[56] References Cited

U.S. PATENT DOCUMENTS

| | | | |
|---|---|---|---|
| 2,299,213 | 10/1942 | Cook et al. ............................. | 260/608 |
| 2,362,624 | 11/1944 | Gaynor et al. .................. | 260/968 X |
| 3,354,240 | 11/1967 | Pochowicz ....................... | 260/930 X |
| 3,737,486 | 6/1973 | Schatze et al. .................. | 260/949 X |

*Primary Examiner*—Anton H. Sutto
*Attorney, Agent, or Firm*—Charles B. Rodman; Roger S. Benjamin

[57] ABSTRACT

The present invention is a process for making thiobisphenol phosphorus acid esters by reacting aryl esters of pentavalent phosphorus acids with sulfur halides. The invention also encompasses groups of novel compounds made by the process.

12 Claims, No Drawings

THIOBISPHENOL ESTERS OF PENTAVALENT PHOSPHORUS ACIDS

This is a continuation, of application Ser. No. 26,060 filed Apr. 6, 1970, now abandoned.

BACKGROUND OF THE INVENTION

The present invention relates to a process for preparing mono, di and polythio-bisphenol phosphorus acid esters. Particularly, the present invention relates to a process for preparing sulfur linked aryl esters of pentavalent phosphorus acids.

More particularly, the present invention relates to a process for preparing compounds which are used as insecticides, lubricant additives, functional fluids, fuel additives, plasticizers and stabilizers for plastics such as PVC, polyethylene and polypropylene, and thermoplastic and thermoset polymers. performance Many types of materials compete to meet the high performance characteristics needed in modern functional fluids. Materials used in this field are petroleum mineral oils, synthetic ester fluids, polyether fluids, silicone fluids, chlorinated biphenyls, and esters and amides of phosphorus.

However, difficulties exist in the application of available materials to functional fluid use because of the extreme operating conditions encountered in modern machinery. To be effective, functional fluids used as lubricants under extreme conditions must be viscous materials.

The need for high viscosity fluids requires the incorporation of polymeric viscosity improvers into the fluids which can give rise to problems of sludging and changes of viscosity under the rigors of time and high shear. Heavy duty applications require the use of load bearing additives to increase the load bearing abilities of the fluids. In addition, the fluids are subject to oxidative breakdown requiring the use of oxidation and corrosion inhibitors in formulations. The wide variety of additives has led to increased formulation difficulties in most functional fluid systems.

Of all the presently commercially available functional fluids the phosphate esters have become the most attractive because of their relatively low cost, flame resistance, moderately low vapor pressure and useful range of viscosity. However, functional fluids based on phosphorus esters have encountered increased formulation difficulties in attempting to extend their properties to meet extreme operating conditions.

It has now been found that new classes of compounds can be provided by a simple and direct synthesis method from readily available starting materials, which compounds generally have good lubricity and load bearing properties, oxidation and corrosion inhibiting properties and excellent compatibility with petroleum and synthetic lubricating oils as well as phosphate based functional fluids.

The present invention can provide thiobisphenol phosphorus acid esters having oligomeric and polymeric character which can be linear or crosslinked. The polymer compounds of the present invention generally range from viscous liquids through gummy rubber-like solids to brittle rosin-like materials.

The present invention also provides a commercially feasible method of incorporating the stable phosphate and phosphonate structure into a polymer chain.

Prior to the present invention, compounds containing two phosphorus acid esters linked by a sulfur atom have been prepared. The preparation of O,O,O', O'-tetramethyl-O,O'-thiobis (2-chloro-p-phenylene)phosphonothioate has been accomplished by a complex reaction procedure. The procedure requires the preparation of a sulfur-linked bis-phenol and then the reaction of the bis-phenol and the O,O-dialkyl phosphoryl halide (Lovell et al., U.S. Pat. No. 3,390,209, issued June 25, 1968). In addition, prior to the present invention, incorporation of a phosphorus moiety into a polymer chain generally involved a complex reaction and produced a material with a low phosphorus content (Caldwell et al., U.S. Pat. No. 3,378,523, issued Apr. 16, 1968).

SUMMARY OF THE INVENTION

According to the present invention a method is provided for preparing compounds of the formula:

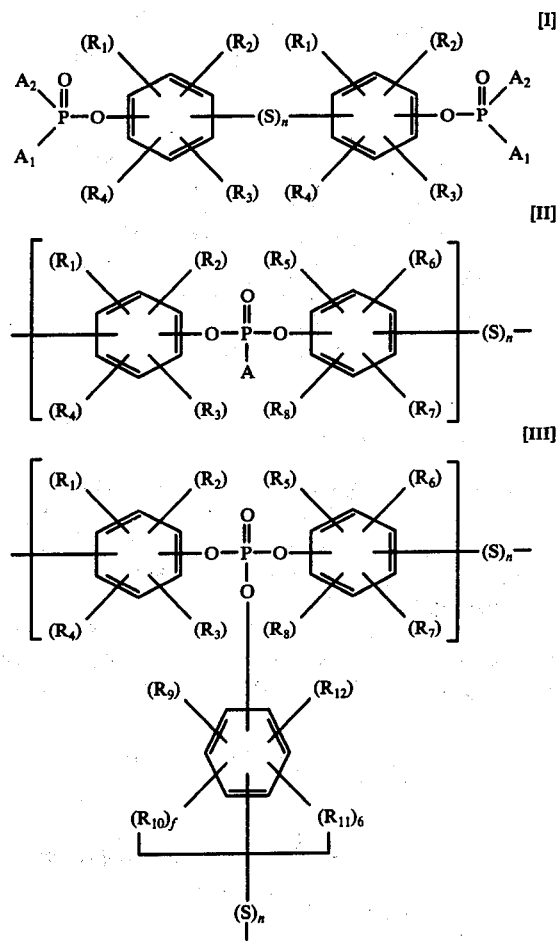

wherein $A_1$ and $A_2$ can be alike or different and can be alkyl, alkoxy, alkaryl, aryl, haloaryl, arylalkyl, aryloxy, alkaryloxy, alkoxyaryl, hydroxy, chlorine, bromine, or

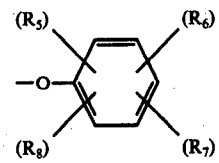

$R_1$, $R_2$, $R_3$, $R_4$, $R_5$, $R_6$, $R_7$, $R_8$, $R_9$, $R_{10}$, $R_{11}$, and $R_{12}$ are independently selected chemically non-interfering substituents attached to the aromatic ring and are selected from the group hydrogen, alkyl, alkoxy, alkaryl, aryl, haloaryl, arylalkyl, aryloxy, alkaryloxy, and halogen and $n$ is an integer having a value of from 1 to about 6 inclusive, comprising reacting a sulfur halide of the formula $(S)_nY_2$ with an aryl ester of a pentavalent phosphorus acid of the formula:

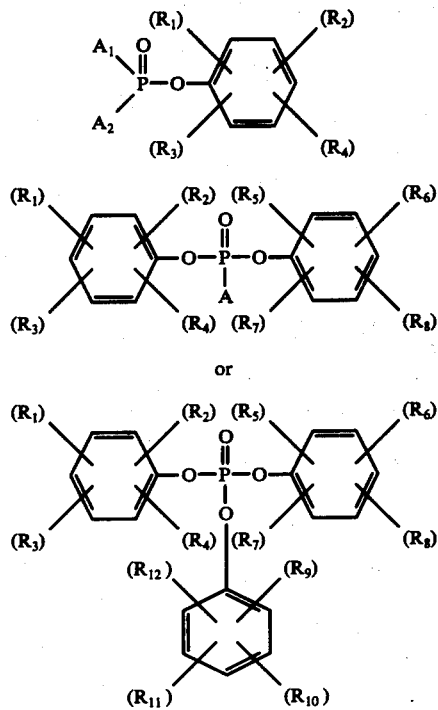

wherein Y is a halogen with an atomic weight between about 33 and about 84, and n, $A_1$, $A_2$, $R_1$, $R_2$, $R_3$, $R_4$, $R_5$, $R_6$, $R_7$, $R_8$, $R_9$, $R_{10}$, $R_{11}$ and $R_{12}$ are as defined above to produce thiobisphenol phosphorus acid esters of the formulas [I], [II], [III].

The compounds of the invention may be used as additives for lubricants, functional fluids, and fuels, as insecticides, plasticizers, stabilizers for plastics and linear and cross-linked polymers.

DETAILED DESCRIPTION OF THE INVENTION

In theory, the reaction of sulfur halides with aryl esters of pentavalent phosphorus is believed to proceed in the following manner to produce thiobisphenol phosphorus acid esters.

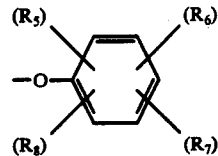

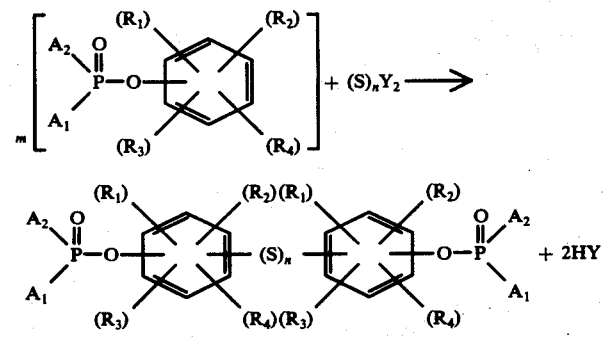

wherein $A_1$, $A_2$, $R_1$, $R_2$, $R_3$, $R_4$ and n are defined as above and Y is a halogen with an atomic weight between about 33 and about 84.

When the phosphorus ester contains more than one aryl group containing a replaceable hydrogen atom, that is, when $A_1$, $A_2$ or both are aryl moieties of the formula:

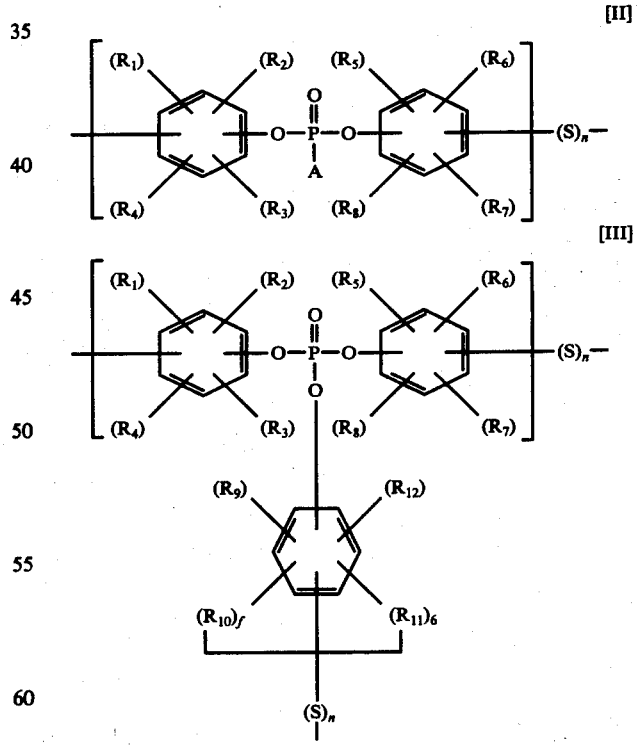

the process of this invention can produce polymeric substances wherein more than two phosphorus acid ester molecules are linked by the $(S)_n$ group. This is accomplished by adjusting the mole ratio of sulfur halide to phosphorus ester to mole ratios greater than 1:2 and reacting under conditions suitable for preparation of the thiobisphonol phosphorus acid esters.

As the mole ratio of sulfur halide to phosphorus ester increases the properties of the products of the process change from viscous oils through tacky gums and rubbery solids to brittle rosin-like material; the highly crosslinked materials are thermoset resins with combustion resistant or self extinguishing properties.

In practice mole ratios of sulfur halide to arylphosphorus acid esters as high as about 3:2 can be useful. The products derived from the use of higher sulfur halide ratios are materials of the repeating formulas:

wherein A, $R_1$, $R_2$, $R_3$, $R_4$, $R_5$, $R_6$, $R_7$, $R_8$, $R_9$, $R_{10}$, $R_{11}$, $R_{12}$, and n are as defined above.

The term thiobisphenol phosphorus acid ester is used herein to denote the products of the process of the present invention wherein two or more aryl esters of pentavalent phosphorus acids are linked by sulfur or polysulfur moieties and which have structural formulas which conform to [I], [II], and [III].

By alkyl is meant the group of monovalent radicals derived from the saturated series of from 1 to about 20 carbon atoms such as methyl, ethyl, propyl, isopropyl, butyl, penty, hexyl, octyl, nonyl, decyl, undecyl, dodecyl, tridecyl, tetradecyl, pentadecyl, hexadecyl, octadecyl, nonadecyl and eicosyl.

The term alkoxy is used herein to describe an alkyl radical as described which is attached to the remainder of the molecule by oxygen; examples of which are methoxy, ethoxy, propoxy, isopropoxy, butoxy, pentyloxy, hexyloxy, heptyloxy, nonyloxy, decyloxy, pentadecyloxy, and eicosyloxy. Although alkyl, and alkoxy moieties containing 20 carbon atoms are useful in the practice of the present invention, it is preferred to utilize moieties containing from 1 to about 14 carbon atoms and most preferably moieties containing from 1 to about 8 carbon atoms.

Aryl is used herein to denote a radical containing not more than two fused rings derived from benzene or substituted benzenes by the removal of a hydrogen atom. Such radicals include but are not limited to phenyl, naphthyl, biphenyl, phenylnaphthyl and the like. Alkaryl is used herein to denote an aryl radical as described herein in which one or more of the hydrogen atoms have been replaced by an alkyl radical. Such radicals include but are not limited to tolyl, xylyl, mesityl, ethylphenyl, propylphenyl, butylphenyl, octylpheny, amylphenyl, nonylphenyl, dodecylphenyl, eicosylphenyl, methylnaphthyl and the like, Haloaryl is intended to denote an aryl radical as described in which one or more of the hydrogen atoms has been replaced by a halogen atom. Included within the definition of haloaryl are radicals such as chlorophenyl, bromophenyl, dichlorophenyl, parachlorotolyl, 4-bromo-o-tolyl, parachloro-octyl-phenyl, and the like.

Arylalkyl, as used herein, denotes an alkyl radical substituted by an aryl radical, such as benzyl, alpha-methylbenzyl, alpha,alpha-dimethylbenzyl, phenylethyl, and the like.

As used herein, aryloxy denotes an aryl radical as described attached to the remainder of the molecule by an oxygen atom. Alkaryloxy, as used herein, denotes an alkaryl radical attached to the remainder of the molecule by an oxygen atom.

As used herein, alkoxyaryl is intended to denote am aryl radical in which one of more hydrogen atoms have been replaced by an alkoxy radical. Examples of alkoxyaryl radicals are propoxy phenyl, ethoxyphenyl, pentoxyphenyl, methoxy naphthyl and the like.

Halogen is used herein to denote fluorine, chlorine, bromine and iodine. The preferred halogens are chlorine and bromine.

The esters of pentavalent phosphorous acids suitable for the practice of this invention are the phosphate, phosphonate or phosphinate type. The pentavalent phosphorus acid esters must contain at least one aryl or substituted aryl group containing at least one replaceable hydrogen atom on the aromatic ring which is attached to the phosphorus through an oxygen link. The aryl ester radical which reacts with the sulfur chloride or bromide must have at least one replaceable hydrogen atom. The aryl radical can be substituted with up to four chemically non-interfering substituents but it is generally preferred to have no more than three substituents on the aromatic ring.

Phosphate, phosphonate and phosphinate are used herein in accordance with "From the Report of the ACS Nomenclature Spelling and Pronunciation Committee for the First Half of 1952", Chemical and Engineering News, Vol. 30 page 4515, Oct. 27, 1952.

Certain substituents when attached to the aromatic ring can interfere with the reaction. Interference occurs when the substituent group is reactive with the sulfur compounds employed in the practice of this invention, such as mercapto, or when the group is strongly electron withdrawing such as nitro.

The following are examples of phosphorus acid esters which can be used as reactants in the practice of this invention. They are included for illustrative purposes only and are not intended to define the limits of compounds suitable for the practice of the invention.

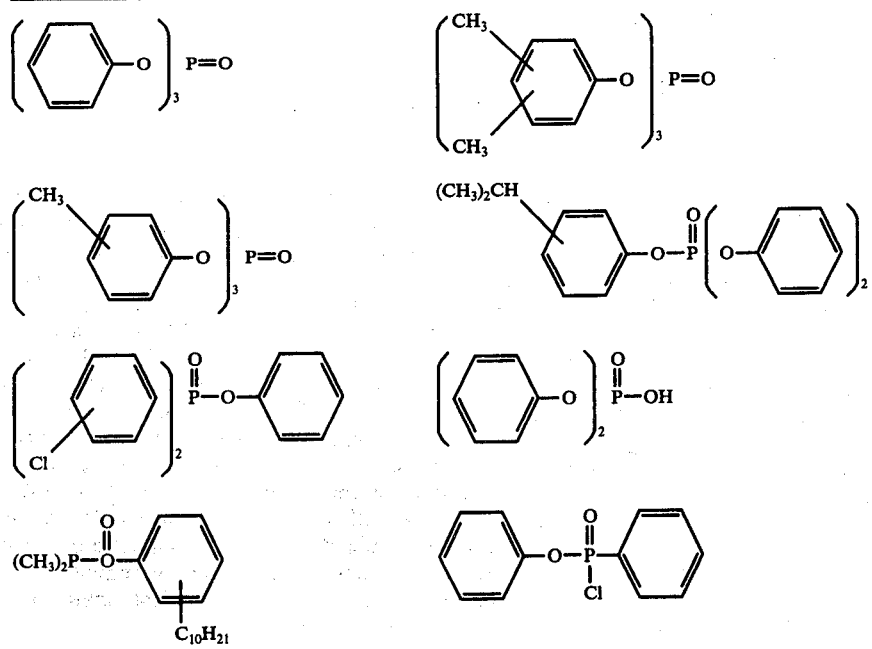

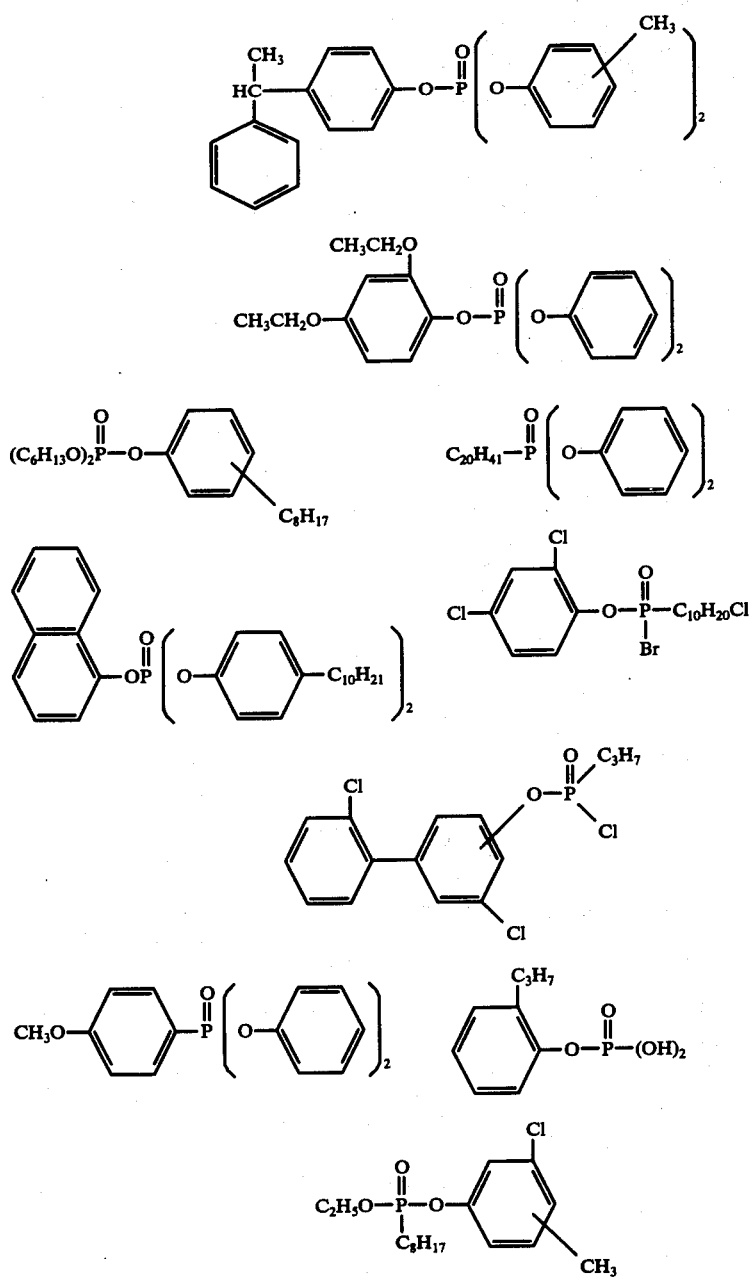

(S)$_n$Y$_2$ is a sulfur compound wherein n is an integer from 1 to about 6 and Y is a halogen with an atomic weight between about 33 and about 84. Illustrative of the sulfur compounds useful in the practice of this invention are sulfur monochloride, sulfur dichloride, sulfur monobromide, sulfur dibromide, and the higher polysulfur dichlorides (dichlorosulfanes) and dibromides. In the practice of the invention, a solution of sulfur in sulfur monochloride or other dihalosulfanes is useful as the equivalent of the higher polysulfur compounds and is to be included within the terms (S)$_n$Y$_2$. As practiced in the invention, up to about 6 sulfur atoms per 2 bromine or chlorine atoms can be employed either as (S)$_n$Y$_2$, of as a solution of sulfur in S$_2$Y$_2$, or as mixed dihalosulfanes averaging S$_6$Y$_2$. Due to its low cost, ready availability and high reactivity sulfur monochloride, sulfur dichloride and solutions of sulfur therein are the preferred reactants for the practice of this invention.

The practice of this invention is preferably though not necessarily conducted in the presence of a catalyst. It is preferred to employ a Freidel-Crafts type catalyst. Friedel-Crafts catalysts are described in Friedel-Crafts and Related Reactions, by George A. Olah, Interscience Publishers, 1963. Ferric chloride is a preferred catalyst although the following are also suitable catalysts: aluminum chloride, zinc chloride, nickel chloride, tin chloride, titanium chloride, zirconium chloride, cobalt chloride, ferric bromide, zinc oxide, molybdenum chloride, and boron trifluoride. Acidic clays such as acidic montmorillonite, alumina, silica gel and acidic aluminosilicates can also be used as catalysts. The catalyst materials are employed in catalytic amounts which range from about 0.05 percent to about 15 percent by weight of the reactants.

The process of this invention can be conducted batchwise or continuously at temperatures from about −20° C. to about 270° C., preferably from about 40° C. to about 200° C., the optimum temperature in any given case depending on the organic reactants. Those reactants having activating substituents such as alkoxy on the aromatic ring can best be reacted near the lower end of the range, whereas those reactants having somewhat deactivating substituents such as halogen may be suitably reacted near the upper end of the temperature range.

The process of this invention can be conveniently conducted in the absence of a solvent, but inert solvents such as carbon tetrachloride, alkanes such as heptane, cycloalkanes such as cyclohexane, chlorohydrocarbons such as ethylene dichloride and tetrachloroethane, nitroalkanes such as nitromethane and nitroethane, unreactive aromatic compounds such as trichlorobenzene or nitrobenzenes and inorganic solvents such as phosphorus oxychloride can be used.

The novel products of this invention can be used in the crude form or can be purified by neutralization, washing, distillation, vacuum distillation or by recrystallization.

It is possible to react mixtures of different aryl esters of pentavalent phosphorous and produce reaction products containing the esters combined in some random manner. That is especially advantageous when crude mixtures of aryl esters of pentavalent phosphorous are reacted with sulfur halides to form additives, antioxidants, plasticizers and polymeric compositions. These reaction products are intended to be encompassed by the present invention.

A group of oil soluble products of this invention are useful as lubricants or lubricant additives exhibiting good load bearing properties and providing wear resisting properties to gears, bearings, and other moving parts.

The products of the reactions of substituted aryl acid phosphates and sulfur chlorides show excellent properties as load bearing additives and are the preferred compounds for this application.

The liquid or oil soluble products of this invention can generally be used alone or in blends with petroleum oils, synthetic ester fluids (lubricants and hydraulic fluids), triaryl phosphate functional fluids, and polyphenyl ether fluids. The liquid products of the invention can also be used as plasticizers for polymers such as polyvinyl chloride. In both the functional fluid and the plastic applications, the products of the invention generally exhibit antioxidant properties.

The liquid polymeric products of this invention, that is, those having at least three phosphate groups per molecule are generally the preferred species for use as viscosity modifiers for oil and as low volatility plasticizers. This viscosity index of these products is considerably higher than the viscosity index of the related triaryl phosphates not containing a sulfur linkage.

As additives to functional fluids of the synthetic ester types the addition of small amounts of the products of the reaction of a mixed substituted triaryl phosphate and a sulfur halide generally show high corrosion inhibiting activity, an increase in the oxidation stability of the mixture, an increase in loading properties and a reduced tendency to form deposits on metal surfaces.

The liquid or oil soluble products of this invention made from substituted triaryl phosphates generally are stable materials imparting oxidation stability and corrosion inhibition, to blends of petroleum oils, synthetic ester fluids (lubricants and hydraulic fluids), triaryl phosphate functional fluids, and polyphenyl ether fluids.

In order that the present invention be more fully understood, the following examples are given by way of illustration. No specific details or enumerations contained therein should be construed as limitations on the present invention except insofar as they appear in the appended claims. All parts and percentages are by weight unless otherwise specifically designated.

EXAMPLE 1

[(C$_6$H$_5$O)$_2$ PO(OC$_6$H$_4$)]$_2$ S

To a mixture of 326 grams (1 mole) of triphenyl phosphate and 0.5 grams of ferric chloride in a flask fitted with a dry ice cooled condenser were added 51.5 grams (0.5 mole) of freshly distilled sulfur dichloride (SCl$_2$). The addition was done at a rate to maintain the temperature of the reactants below 80° C. After the addition was complete, the temperature was raised to 120° C. and maintained at this level until the evolution of hydrogen chloride ceased (about 48 hours). The reaction mixture was freed of volatile material by application of vacuum. The reaction mixture was washed with dilute hydrochloric acid, dilute sodium hydroxide and then water. After drying under a vacuum of 1 millimeter of mercury, a clear, tan, oil product was obtained having an index of refraction at 25° C. of 1.5932, and a viscosity of 583 S.U.S. (Saybolt Universal Seconds) at 100° F.

| Calculated for: | C$_{36}$H$_{28}$O$_8$P$_2$S |
|---|---|
| Theoretical S: | 4.5% |
| Found S: | 4.5% |

EXAMPLE 2

[(C$_6$H$_5$O)$_2$ PO(OC$_6$H$_4$)]$_2$ S$_2$

To 326 grams (1 mole) of triphenyl phosphate and 0.5 grams of ferric chloride in a flask at 70° C. were added 67.5 grams (0.5 mole) of sulfur monochloride (S$_2$Cl$_2$). The temperature was increased to 140° C. and then the reaction mass was cooled to 120° C. and held at this temperature until hydrogen chloride evolution ceased (about 12 hours). The reaction mixture was freed of volatile material by application of vacuum and then washed with dilute hydrochloric acid, dilute sodium hydroxide, and then water. After drying under a vacuum of 1 millimeter of mercury the product was a clear, reddish-brown oil having an index of refraction at 25° C. of 1.6106.

| Calculated for: | C$_{36}$H$_{28}$O$_8$P$_2$S$_2$ |
|---|---|
| Theoretical S: | 8.96% |
| Found S: | 8.91% |

EXAMPLE 3

[(C$_6$H$_5$O)$_2$ PO(OC$_6$H$_4$)]$_2$ S$_3$

A solution of 16 grams (0.5 mole) of sulfur in 67.5 grams (0.5 mole) of sulfur monochloride was added to 326 grams (1 mole) of triphenyl phosphate and 0.5 grams of ferric chloride at 60° C. The mixture was heated to 115° C. and held at this temperature until the hydrogen chloride evolution was complete. The reaction mixture was freed of volatile material by application of vacuum, then washed with dilute hydrochloric acid and then with water. After drying under a vacuum at 1 millimeter of mercury the product was a reddish oil having an index of refraction at 25° C. of 1.6226.

| Calculated for: | $C_{36}H_{21}O_8P_2S_3$ |
|---|---|
| Theoretical S: | 12.9% |
| Found S: | 12.7% |

EXAMPLE 4

To 326 grams (1 mole) of triphenyl phosphate and 0.5 grams of ferric chloride at 65° C. were added 135 grams (1 mole) of sulfur monochloride ($S_2Cl_2$). The reaction mixture was heated to 115° - 134° C. After 4 hours when 1.55 mole of hydrogen chloride had evolved, the product was found to be a resilient, clear yellowish, thermoplastic resin, soluble in toluene, and when deposited from toluene affording a transparent adherent coating on a steel surface.

Continued heating of this polymer at 160° C. caused it to thermoset (become insoluble in organic solvents). The polymer was a brittle reddish material which was self-extinguishing when ignited. It could be pulverized and blended into a resin such as polyethylene as an inert non-plasticizing filler which imparts slow burning properties to the blend at loadings of from 5 to 50%.

EXAMPLE 5

To 180 grams (0.5 mole) of diphenyl p-chlorophenyl phosphate and 0.5 grams of ferric chloride was added 68 grams (0.5 mole) of sulfur monochloride. The mixture was heated at 115° - 135° C. for 6 hours. The product was a tough, slightly flexible, non-flammable resin.

EXAMPLE 6

To 326 grams (1 mole) of triphenyl phosphate and 0.5 grams of ferric chloride at 60° C. were added 89.4 grams (0.667 moles) of sulfur monochloride. The reaction mixture was held at 120° C. until the evolution of hydrogen chloride had ceased (about 20 hours). The reaction mixture was freed of volatile material by application of vacuum, then washed with dilute hydrochloric acid and then water. After drying under vacuum at 1 millimeter of mercury the product was a viscous oil with an index of refraction at 25° C. of 1.6255.

| Calculated for: | $C_{54}H_{41}O_{12}P_2S_4$ |
|---|---|
| Theoretical S: | 11.6% |
| Found S: | 11.3% |

EXAMPLE 7

$[(C_8H_9O)_2 PO(OC_8H_8)]_2 S$

To 205 grams (0.5 mole) of a commercial trixylenyl phosphate and 0.5 grams of ferric chloride at 115° C. were added 25.7 (0.25 mole) of sulfur dichloride ($SCl_2$). After 8 hors the reaction mixture was degassed under vaccum, washed with dilute hydrochloric acid, dilute sodium hydroxide and with water, then dried over magnesium sulfate and filtered. The product was a clear, reddish oil, with a viscosity of 3320 Saybolt Universal Seconds at 100° F.

| Calculated for: | $[(C_8H_9O)_2POOC_8H_8)]_2S$ |
|---|---|
| Theoretical S: | 3.77% |
| Found S: | 3.2% |

EXAMPLE 8

$[(C_6H_5O)_2 PO(OC_7H_6)]_2 S$

To 340 grams (1 mole) of a commercial triaryl phosphate made from a phenol /m-cresol/ p-cresol mixture were added 51.4 grams (0.5 mole) of sulfur dichloride ($SCl_2$) and 1 gram of ferric chloride at 100° - 120° C. The mixture was heated for 12 hours at 100° C. The reaction mixture was degassed under vacuum, washed with dilute hydrochloric acid, dilute sodium hydroxide and with water, then dried at a 1 millimeter of mercury vacuum. The product was a brownish oil with a viscosity of 1114 Saybolt Universal Seconds at 100° F. and an index of refraction at 25° C. of 1.5894.

| Calculated for: | $[(C_6H_5O)_2PO(OC_7H_6)]_2S$ |
|---|---|
| Theoretical S: | 4.5% |
| Found S: | 4.1% |

An analogous run using 10 grams of zinc chloride as a catalyst in place of the ferric chloride catalyst affords a similar product.

EXAMPLE 9

$[(C_6H_5O)_2 PO (OC_7H_6)]_2 S_2$

To 340 grams (1 mole) of a commercial triaryl phosphate made from a phenol /m-cresol/ p-cresol mixture and 0.5 grams of ferric chloride were added 67.5 grams (0.5 mole) of sulfur monochloride ($S_2Cl_2$). Slow hydrogen chloride evolution was noted at 80° C. After 12 hours at 80° C., 0.56 mole of hydrogen chloride has evolved. The reaction was completed by heating at 110° C. for 12 hours. The reaction mixture was degassed under vacuum and then washed with dilute hydrochloric acid, sodium bisulfite, water, dilute caustic soda, and then water. The product was dried by heating at 0.3 millimeter vacuum to obtain a viscous reddish oil with a viscosity of 4,290 Saybolt Universal Seconds at 100° F., 145.5 Saybolt Universal Seconds at 210° F., viscosity index 39, and an index of refraction at 25° C. of 1.6061.

| Calculated for: | $[(C_6H_5O)_2PO—OC_7H_6)]_2S_2$ |
|---|---|
| Theoretical S: | 8.65% |
| Found S: | 8.20% |

EXAMPLE 10 to 978 grams (3 mole) of triphenyl phosphate and 1.5 grams of ferric chloride in a flask fitted with a dry ice cooled condenser were added 139.1 grams (1.35 mole) of freshly distilled sulfur dichloride. The freshly distilled sulfur dichloride was added at a rate to maintain the temperature of the reaction mixture below 80° C. The temperature was raised to 120° C. and maintained at this level until the evolution of hydrogen chloride ceased. The product was degassed under a vacuum, washed with dilute phosphoric acid and then washed with water. The product was dried at 1 millimeter of mercury vacuum to obtain a clear brownish oil with an index of refraction at 25° C. of 1.5895 with a sulfur content of 4.6 percent.

EXAMPLE 11

To 200 grams of phenyl acid phosphate of composition $(C_6H_5O)_{1.47}$ PO $(OH)_{1.53}$ and 1.5 grams of ferric chloride were added 51.5 grams (0.5 mole) of redistilled sulfur dichloride. The mixture was heated at 100° C. for 24 hours. A vacuum was applied to remove volatile materials, leaving a syrupy residue of 222.5 grams. The crude product was boiled with 500 grams of methylene chloride and the resultant solution was decanted from the undissolved viscous liquid. The undissolved material was freed of methylene chloride and amounted to 120 grams. It was found to have the approximate composition $(HO)_2 \overset{O}{\underset{\|}{P}} - O - (C_6H_4)S(C_6H_4)O\overset{O}{\underset{\|}{P}}(OH)_8$ by titration.

The neutralization equivalent

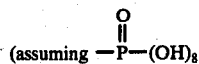

(assuming $-\overset{O}{\underset{\|}{P}}-(OH)_8$ titrates as a monobasic acid to a congo red end point) was as follows:

Calculated: 189 $\frac{Milligrams}{milliequivalent}$ Found: 194 $\frac{Milligrams}{milliequivalent}$ The methylene chloride solution was filtered through charcoal and clay and the methylene chloride evaporated at 100° C. and 20 millimeters of mercury pressure to obtain about 100 grams of a yellow syrup having the approximate composition $(C_6H_5O)P(O)(OH)—(OC_6H_4)—S—(C_6H_4O) O—POOH—(OC_6H_5)$. The neutralization equivalent was as follows:

Calculated: 262 $\frac{Milligrams}{milliequivalent}$ Found: 266 $\frac{Milligrams}{milliequivalent}$ The methylene chloride soluble fraction was found to be soluble in an ester based Type I aviation gas turbine lubricant and improved the load bearing properties and the oxidation resistance at concentration of 0.02 to 0.2% by weight.

EXAMPLE 12

Octylphenyl acid phosphate is reacted with $SCl_2$ under the conditions of the previous example to form:

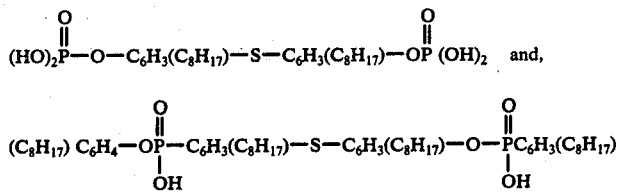

Both compounds are found to be soluble in an ester base Type I aviation gas turbine lubricant and are found to improve oxidation resistance and load bearing properties.

EXAMPLE 13

To a mixture of 20 grams of mixed mono and diphenyl acid phosphate, prepared by reacting phenol and phosphorus pentoxide, and 0.2 grams of ferric chloride were added 5.7 grams of commercial sulfur dichloride (70% $SCl_2$, 30% $S_2Cl_2$). The mixture was heated gradually to 100° C., and heated under reflux for 5 hours. The product mixture was leached with hot methylene chloride. The methylene chloride was evaporated from the extract to obtain an oil having a neutralization equivalent of 227 milligrams per milliequivalent and a sulfur content of 7.8% corresponding to a mixture of $(C_6H_5O)\overset{O}{\underset{\|}{P}} (OH) (OC_6H_4)S_{3\cdot 2}(C_6H_4O)\overset{O}{\underset{\|}{P}}(OH) (OC_6H_5)$ and $(HO)_2\overset{O}{\underset{\|}{P}} OC_6H_4S_{1.2}C_6H_4O\overset{O}{\underset{\|}{P}}(OH)_2$.

Examples of additional compounds which are prepared by the practice of this invention appear in Table I. These compounds can be prepared by use of equipment and methods described in the prior examples.

Results of tests conducted on products of this invention are included herein to exhibit the utility of these materials.

Wear Testing

Small portions of the products of the reaction of aryl phosphates and sulfur chloride were added to a Type I aviation gas turbine lubricant composed of 67 – 68.5% by weight of trimethylolpropane triheptanoate, 30% by weight of di-2-ethylhexyl adipate, the remaining portion being made up of oxidation and corrosion inhibitors. The mixtures were tested according to ASTM (American Society of Testing Materials)-D2266 at 600 RPM for 1 hour at 75° C. (commonly known as the Four Ball Wear Test). Results of the test are shown in Table II.

TABLE I

| Ex. No. | Phosphorus Compound (2 moles) | Sulfur Halide (1 mole) | Catalyst | Temp. | Principle Product (plus HCl) |
|---|---|---|---|---|---|
| 14 | $(\bigcirc\!\!-\!O)_2 \overset{O}{\underset{\|}{P}} OC_8H_{17}$ | $SCl_2$ | 1% $TiCl_4$ | 120° C. | 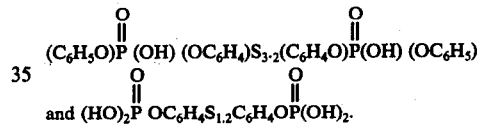 |

TABLE I-continued

| Ex. No. | Phosphorus Compound (2 moles) | Sulfur Halide (1 mole) | Catalyst | Temp. | Principle Product (plus HCl) |
|---|---|---|---|---|---|
| 15 | C₆H₅—OPCl₂ (with =O) | SCl₂ | 0.2% FeCl₃ | 110° C. | Cl₂PO—C₆H₄—S—C₆H₄—OPCl₂ (with =O groups) |
| 16 | C₆H₅—OP(OH)₂ (with =O) | S₂Cl₂ | 0.2% FeCl₃ | 115° C. | (HO)₂PO—C₆H₄—S₂—C₆H₄—OP(CH)₂ (with =O) |
| 17 | (C₆H₅)₂P(O—C₆H₅) (with =O) | S₂Cl₂ | 1% SnCl₄ | 140° C. | (C₆H₅O)(C₆H₅)PO—C₆H₄—S₂—C₆H₄—OP(C₆H₅)(O—C₆H₅) |
| 18 | (2-Cl-C₆H₄—O)₃P (with =O) | S₂Cl₂ | 1% FeCl₃ | 140° C. | (2-Cl-C₆H₄—O)₂PO—C₆H₃Cl—S₂—C₆H₃Cl—OP(O—C₆H₄-Cl)₂ |
| 19 | (CH₃)₂PO—C₆H₄—C(CH₃)₃ (with =O) | S₂Cl₂ | 0.5% FeCl₃ | 100° C. | (CH₃)₂PO—C₆H₃—C(CH₃)₃(CH₃)₃C—C₆H₃—OP(CH₃)₂ bridged by S₂ |
| 20 | CH₃P(O—C₆H₅)₂ (with =O) | S₂Cl₂ | 1% SbCl₃ | 80° C. | (CH₃)(C₆H₅—O)P(O—C₆H₄—S₂—C₆H₄—O)P(O—C₆H₅)(CH₃) |
| 21 | (C₆H₅—O)₃P=O | S₆Cl₂ (4S+S₂Cl₂) | 0.5% FeCl₃ | 110° C. | (C₆H₅—O)₂P—O—C₆H₄—S₆—C₆H₄—OP(O—C₆H₅)₂ |
| 22 | (CH₃O—C₆H₄—O—)₃P=O | S₂Cl₂ | 0.5% ZnCl₂ | 75° C. | (CH₃O—C₆H₄—O)₂P—O—C₆H₃(OCH₃)—S₂—C₆H₃(OCH₃)—O—P(O—C₆H₄—OCH₃)₂ |
| 23 | (CH₃O)₂P—O—C₆H₅ (with =O) | S₃Cl₂ (S+S₂Cl₂) | 0.5% FeCl₃ | 100° C. | (CH₃O)₂P—O—C₆H₄—S₃—C₆H₄—O—P—(OCH₃)₂ |

TABLE II

| Reaction Product Additive | Concentration | Scar Diameter (millimeters) in Four Ball Wear Test ASTM D2,266,600 RPM., 75° C. - 1 Hour (10Kg.) | (40Kg.) |
|---|---|---|---|
| None | — | 0.56 | 0.85 |
| Product of Ex. 1 | 2% | 0.24 | 0.34 |
| Product of Ex. 8 | 2% | 0.21 | 0.41 |
| Product of Ex. 9 | 2% | 0.24 | 0.40 |
| Product of Ex. 13 | 1% | | 0.38 |
| Product of Ex. 13 | 0.1% | | 0.39 |

The results of the four ball wear tests shows that the products tested all show activity as antiwear additives for the functional fluids.

Table III is a comparison of the properties of the product of Example 10 with a commercially prepared trixylenyl phosphate.

TABLE III

| | | Product Example 10 | Trixylenyl Phosphate |
|---|---|---|---|
| Viscosity | S.U.S.* (98.8° C.) | 54.65 | 45.1 |
| | C.S.** (98.8° C.) | 8.64 | 4.75 |
| | S.U.S.* (37.77° C.) | 370.3 | 312 |
| | C.S.** (37.77° C.) | 79.96 | 67.4 |
| | S.U.S.* (−1.11° C.) | 14296 | 31534 |
| | C.S.** (−1.11° C.) | 3093 | 6803 |

TABLE III-continued

| | Product Example 10 | Trixylenyl Phosphate |
|---|---|---|
| Viscosity Index | 85 | −50 |
| Auto Ignition Temp. ° C. | 699 | 677 |
| Hot Manifold Temp. ° C. | 788 | 705 |

*S.U.S. - Saybolt Universal Seconds
**C.S. - Centistokes

The oxidation and corrosion inhibiting properties of the reaction products of this process were tested according to Federal Test Standard 791a, Method 5308.5 for 72 hours at 197.2° C. The metal specimens used were as follows:

| Copper (electrolytic) | **QQ-C-576 |
|---|---|
| Steel (mild) | **QQ-S-698 |
| Aluminum Alloy | **QQ-A-255 T-4/T-5 |
| Magnesium Alloy | **QQ-M-44 |

**Federal Specification Number, Index of Federal Specifications and Standards, January 1, 1968, General Services Administration Federal Supply Service.

The results of the oxidation and corrosion tests of the product of Example 8 as an additive are shown in Table IV. The product of Example 8 was added in two levels to the Type I aviation gas turbine lubricant previously described and compared to the properties of the lubricant without the product additive.

TABLE IV

| Test Number | 1 | 2 | 3 |
|---|---|---|---|
| Composition | | | |
| Type I Aviation Gas Turbine Lubricant Percent | 100 | 99.5 | 98 |
| Product of Example 8 Percent | | 0.5 | 8.0 |
| Fluid Properties | | | |
| Viscosity at 98.8° C.C.S.* | 3.54 | 3.6 | 3.64 |
| Viscosity at 377.77° C.C.S.* | 14.31 | 14.87 | 15.30 |
| Viscosity at −53.88° C.C.S.* | 11,500 | 11,663 | 12,976 |
| Acid No. Milligrams KOH/Gram | 0.25 | 0.25 | 0.29 |
| Four Ball Wear Test, Millimeters Scar 40 Kg, 600 RPM, 75° C., 1 hour | 0.8 | 0.57 | 0.4 |
| Oxidation-Corrosion Stability (72 hours at 197.2° C.) | | | |
| Fluid Property Changes | | | |
| Viscosity at 377.77° C. Percent | +31.7 | +13.4 | +4.13 |
| Acid No., Milligram KOH/Gram Percent | +12.4 | +9.88 | +3.53 |
| Metal Weight Changes, Milligrams/Square Centimeter | | | |
| Magnesium | −8.73 | −0.100 | −0.300 |
| Copper | −0.308 | −0.062 | −0.154 |
| Steel | 0.00 | 0.00 | 0.00 |
| Aluminum | 0.00 | 0.00 | 0.00 |

*Centistokes

The preceding examples indicate the variety of compounds which can be produced by the method of the present invention. The products are compounds which are produced by the simple reaction disclosed and are useful in many areas of commerce.

What is claimed is:

1. A process for the preparation of polymeric phosphorus acid esters comprising: reacting an aryl ester of a pentavalent phosphorus acid of the formula:

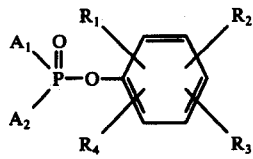

with a sulfur compound of the formula $S_nY_2$, in a ratio of less than or equal to about 1.5:1 wherein $A_1$ and $A_2$ are independently selected from the group consisting of alkyl, alkoxy, aryl, alkaryl, haloaryl, arylalkyl, alkoxyaryl, alkaryloxy, aryloxy, hydroxy, chlorine, bromine and

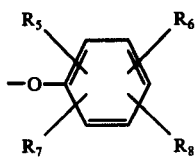

each of said alkyl, alkoxy, aryl, alkaryl, haloaryl, arylalkyl, alkoxyaryl, alkaryloxy, and aryloxy groups having from 1 to 20 carbon atoms; $R_1$, $R_2$, $R_3$, $R_4$, $R_5$, $R_6$, $R_7$, and $R_8$ are independently selected from the group consisting of hydrogen, alkyl, alkoxy, aryl, alkaryl, haloaryl, arylalkyl, aryloxy, and halogen; each of said alkyl, alkoxy, aryl, alkaryl, haloaryl, arylalkyl, and aryloxy groups having from 1 to 20 carbon atoms, Y is a halogen of atomic weight between 33 and about 84 and n is an integer having a value of from 1 to about 6 inclusive; said reaction being conducted in the presence of a Friedel-Crafts catalyst.

2. The process of claim 1 wherein $A_2$ is

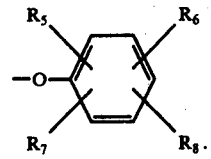

3. The process of claim 1 wherein $A_1$ and $A_2$ are

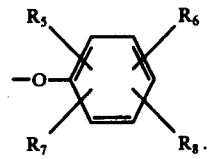

4. The process as defined in claim 2 conducted in the presence of a ferric chloride catalyst.

5. The process as defined in claim 2 conducted in the presence of a zinc chloride catalyst.

6. The process of claim 2 wherein the sulfur compound is sulfur chloride.

7. The process of claim 2 conducted at a temperature of from about 40° to about 200° C.

8. The process as defined in claim 3 conducted in the presence of a ferric chloride catalyst.

9. The process as defined in claim 3 conducted in the presence of a zinc chloride catalyst.

10. The process as defined in claim 3 wherein the sulfur compound is sulfur chloride.

11. The process of claim 3 conducted at a temperature of from about 40° to about 200° C.

12. Polymeric compositions of the repeating unit:

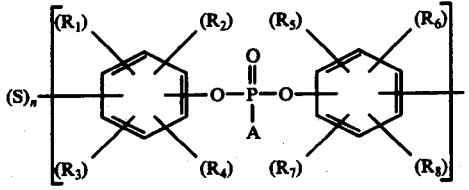

wherein A is aryloxy, and $R_1$, $R_2$, $R_3$, $R_4$, $R_5$, $R_6$, $R_7$, and $R_8$ are independently selected from the group consisting of hydrogen and halogen, and $n$ is an integer having a value of from 1 to about 2.

* * * * *

UNITED STATES PATENT AND TRADEMARK OFFICE
CERTIFICATE OF CORRECTION

PATENT NO. : 4,051,201
DATED : September 27, 1977
INVENTOR(S) : Edward D. Weil

It is certified that error appears in the above-identified patent and that said Letters Patent are hereby corrected as shown below:

Col. 1, Line 18, "polymers. performance" should read --polymers.--

Col. 4, Line 22, "thiobisphonol" should read --thiobisphenol--

Cols. 2 and 4, Lines 48 and 58, in the Formula, "$(R_{11})_6$" should read --$(R_{11})_e$--

Col. 5, Line 5, "saturated series" should read --saturated aliphatic series--

Col. 5, Line 7, "penty" should read --pentyl--

Col. 6, Line 6, "am" should read --an--

Col. 7, Line 65, "of" should read --or--

Col. 9, Lines 29 and 31, "phosphorous" should read --phosphorus--

Col. 9, Line 59, "This" should read --The--

Col. 11, Line 52, in the Table, Calculated for:, "$C_{54}H_{41}O_{12}P_2S_4$" should read --$C_{54}H_{41}O_{12}P_3S_4$--

Col. 11, Line 63, "8 hors" should read --8 hours--

Col. 12, Line 14, "100°C." should read --110°C.--

Col. 12, Line 38, "has" should read --had--

UNITED STATES PATENT AND TRADEMARK OFFICE
CERTIFICATE OF CORRECTION

PATENT NO. : 4,051,201
DATED : September 27, 1977
INVENTOR(S) : Edward D. Weil

It is certified that error appears in the above-identified patent and that said Letters Patent are hereby corrected as shown below:

Col. 13, Line 28, in the Formula, ..."$\overset{O}{\underset{\|}{O}}P(OH)_8$ by titration." should read ...--$\overset{O}{\underset{\|}{O}}P(OH)_2$ by titration.--

Col. 13, Line 34, in the Formula, ..."$(OH)_8$" should read ...--$(OH)_2$--

Col. 14, Line 34, in the Formula, ..."$S_{3.2}$"... should read ...--$S_{1.2}$--...

Col. 17, Line 10, in Table IV, Col. 3, Product of Example 8 Percent, "8.0" should read --2.0--

Col. 17, Lines 12 and 17, in Table IV, Viscosity at, "377.77°" should read --37.77°--

Col. 17, Line 12, in Table IV, Col. 3, "15.30" should read --15.00--

Signed and Sealed this

Thirteenth Day of June 1978

[SEAL]

Attest:

RUTH C. MASON
Attesting Officer

DONALD W. BANNER
Commissioner of Patents and Trademarks